United States Patent
Fink et al.

(10) Patent No.: US 9,283,295 B2
(45) Date of Patent: Mar. 15, 2016

(54) ADD ON FILTER AND AIR FILTRATION SYSTEM AND METHOD

(71) Applicant: RGF Environmental Group, Inc., Riviera Beach, FL (US)

(72) Inventors: Ronald G. Fink, Jupiter, FL (US); Walter B. Ellis, Jupiter, FL (US)

(73) Assignee: RGF ENVIRONMENTAL GROUP, INC., Riviera Beach, FL (US)

( * ) Notice: Subject to any disclaimer, the term of this patent is extended or adjusted under 35 U.S.C. 154(b) by 396 days.

(21) Appl. No.: 13/750,876

(22) Filed: Jan. 25, 2013

(65) Prior Publication Data
US 2014/0212327 A1    Jul. 31, 2014

(51) Int. Cl.
*A61L 9/00*    (2006.01)
*A61L 9/20*    (2006.01)
*B01D 46/00*    (2006.01)

(52) U.S. Cl.
CPC ... *A61L 9/00* (2013.01); *A61L 9/20* (2013.01); *B01D 46/0028* (2013.01); *A61L 2209/14* (2013.01); *Y10T 29/49826* (2015.01)

(58) Field of Classification Search
CPC ......... B01D 46/0028; A61L 9/00; A61L 9/20
USPC .................................................. 422/120, 121
See application file for complete search history.

(56) References Cited

U.S. PATENT DOCUMENTS

| | | | | |
|---|---|---|---|---|
| 3,744,216 | A * | 7/1973 | Halloran | 96/16 |
| 5,334,347 | A * | 8/1994 | Hollander | 422/24 |
| 6,500,387 | B1 * | 12/2002 | Bigelow | 422/24 |
| 2008/0112845 | A1 * | 5/2008 | Dunn et al. | 422/24 |
| 2013/0189162 | A1 * | 7/2013 | Jeong | 422/121 |

* cited by examiner

*Primary Examiner* — Kevin Joyner
(74) *Attorney, Agent, or Firm* — Rothwell, Figg, Ernst & Manbeck, P.C.

(57) ABSTRACT

The present invention relates to an add on filter and air filtration system and method incorporating an add on filter for applying ultraviolet light to an environment to create oxidizing agents for killing microbes, such as bacteria, mold, and viruses, and for destroying odors. The add on filter may be coupled to existing air filtration systems to provide further filtration of the air. The add on filter includes an ultraviolet light source for emitting a broad spectrum of ultraviolet light and a catalytic target structure mechanically coupled to the ultraviolet light source. The system and method result in the production of Hydroxyl Radicals, Super Oxide ions and Hydro Peroxide for killing microbes.

17 Claims, 13 Drawing Sheets

ADD ON FILTER AND AIR FILTRATION SYSTEM AND METHOD

TECHNICAL FIELD

The present invention relates generally to the field of air filtration and, more particularly, to an add on filter and air filtration system and method incorporating an add on filter for applying ultraviolet light to an environment to create oxidizing agents for killing microbes, such as bacteria, mold, and viruses, and for destroying odors.

BACKGROUND

Traditional air filtration systems include filters designed to trap particulates. Particulates are tiny particles suspended in the air. Common particulates include residential pollen, dust mites, dust, smoke and dander (skin flakes). However, there are other types of indoor pollutants, such as microbials and gases. Microbials are bacteria, germs, viruses, fungi, spores and mold. Although bacteria are small in size and usually microscopic, they have an amazing ability to do damage to all living organisms including humans. Many everyday illnesses are also caused by viruses like the common cold or the flu. Mold can be a dangerous allergen, cause infections, and destroy property requiring extensive repair and rebuilding. Traditional air filtration systems are not effective at treating many such microbials and gases.

Indoor odors, caused by things like pets, cooking, garbage, etc., exist in every home and office. Gases, such as benzene, formaldehyde, chloroform, hydrogen sulfide, ammonia, etc., are released from furniture, cabinets, carpets, cleaning chemicals, insulation, insect sprays, hair sprays, etc. Manufactures use chemicals to make these products and they come off as gas into the air in homes and offices. Traditional air filtration systems are not effective at treating such gases.

Microbials cannot be trapped by the filters in traditional air filtration systems. Microbials must be killed in order to cleanse the air supply. Hydroperoxides are very effective at destroying harmful microbials in the air and on surfaces through a process called cell lysing or by changing its molecular structure. Hydroperoxides are also effective at rendering gases harmless by changing its molecular structure.

Therefore, a need exists to further treat air that has been treated by traditional air filtration systems to neutralize the various deleterious effects caused by such microbials and gases. The present invention addresses the shortcomings of traditional air filtration systems and methods.

SUMMARY

Particular embodiments of the present invention are directed to an add on filter and an air filtration system and method incorporating such an add on filter for applying ultraviolet light to an environment to create oxidizing agents for killing microbes, such as bacteria, mold, and viruses, and for destroying odors.

According to particular embodiments of the present invention, an add on filter comprises a first cartridge including an ultraviolet light source for emitting a broad spectrum of ultraviolet light and a catalytic target structure mechanically coupled to the ultraviolet light source. The add on filter may include a box frame configured to be coupled with an intake side of an air handler and may be further configured to house the first cartridge.

In some embodiments, the add on filter also includes a second cartridge. The second cartridge can include a pleated filter, charcoal, sulfur coated carbon or potassium permanganate coated carbon.

In some embodiments, the add on filter further includes a plurality of faces and at least one of the plurality of faces is adjustable between an open and closed position. In some embodiments, the first cartridge is capable of being removed from or placed into the box frame when the adjustable face is in an open position. In some embodiments, the add on filter includes a second cartridge, and the first cartridge and the second cartridge are capable of being removed from or placed into the box frame when the adjustable face is in an open position.

In some embodiments, the catalytic target structure of the add on filter includes a plurality of fin elements.

In some embodiments, the add on filter also includes a ballast configured to provide power to the ultraviolet light source. The ballast can include a power connector configured to receive power from an external source and at least one of the plurality of faces of the box frame includes an opening configured to expose the power connector.

In some embodiments, the box frame is configured to mate with an evaporator unit.

According to particular embodiments of the present invention, the box frame includes two rails positioned on opposite sides of the box. The first end of each of the rails is pivotably coupled to an interior side of a face of the box frame and each of the rails is configured to support the first cartridge. The box frame can include a latch adjustable between a locked position, in which the first cartridge and rails are held in place, and an open position in which the rails are pivotable.

In some embodiments, the box frame is comprised of insulative material.

According to particular embodiments of the present invention, a filter system includes an evaporator including an input end and an output end and an add on filter including an input end and an output end. The add on filter includes a box frame and a first cartridge including an ultraviolet light source for emitting a broad spectrum of ultraviolet light and a catalytic target structure mechanically coupled to the ultraviolet light source. The output end of the add on filter is coupled to the input end of the evaporator. The filter system also includes an air supply including an output end. The output end of the air supply is coupled to the input end of the add on filter.

In some embodiments, the air supply includes a structure carrying air returned from a building.

In another aspect, certain embodiments of the present invention are directed to a method for installing an add on filter in a filter system comprising the steps of coupling an output end of the add on filter described above to an Input end of an evaporator.

The method further includes the steps of coupling an input end of the add on filter to an output end of a return air supply structure and coupling an output end of the evaporator to an air supply structure.

In some embodiments, the method further includes the step of removing a portion of the air supply structure equivalent to a height of the add on filter prior to coupling the output end of the evaporator to the air supply structure.

In another aspect, certain embodiments of the present invention are directed to a method of filtering air comprising the steps of supplying air to an intake structure coupled to the add on filter and providing air to the add on filter. The method further includes the steps of producing an advanced oxidation product with an ultraviolet light and treating the air by killing microbes with the advanced oxidation product. The method also includes the steps of providing the treated air from the add on filter to an evaporator for further treatment and providing the treated air to an air supply.

In some embodiments, the method further includes the step of providing air to a second filter disposed in the add on filter for further filtering.

BRIEF DESCRIPTION OF THE DRAWINGS

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein. In the drawings, like reference numbers indicate identical or functionally similar elements.

DETAILED DESCRIPTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art. Further, the terms and phrases used herein are not intended to be limiting; but rather, to provide an understandable description of the invention.

According to particular embodiments of the present invention, an add on filter for an air filtration system includes a box frame housing a first cartridge. The add on filter may be coupled to existing air filtration systems to provide further filtration of the air. The first cartridge of the add on filter includes an ultraviolet light source for emitting a broad spectrum of ultraviolet light and a catalytic target structure mechanically coupled to the ultraviolet light source. The target catalytic structure comprises a multi-metallic catalytic and hydrophilic material, and the hydrophilic surface attracts and absorbs moisture from the surrounding air. The broad spectrum ultraviolet light include two bands of ultraviolet light at about 254 nm wavelength and at about 185 nm wavelength. The ultraviolet energy at 254 nm strikes the target structure and activates production of Hydroxyl Radicals, Super Oxide ions and Hydro Peroxide on the surface. The ultraviolet energy at 185 nm is sufficient to split oxygen molecules to form ozone gas. These ozone molecules in the air are then reduced back to oxygen via decomposition process initiated by the 254 nm ultraviolet light energy, which results in the production of Hydroxyl Radicals, Super Oxide ions and Hydro Peroxide similar to the surface reaction. This process is described in further detail in co-owned U.S. Pat. No. 7,988,932, the entire disclosure of which is herein incorporated by reference.

FIGS. 1-5 illustrate an add-on filter according to particular embodiments of the present invention. The add on filter 100 includes a box frame 102, a first cartridge 104 and a second cartridge 106. The box frame 102 includes a plurality of walls and is configured to house the first cartridge 104 and the second cartridge 106. The box frame 102 is insulted and includes a plurality of faces or walls. The box frame 102 includes first opening in a first wall and a second opening in a second wall opposite the first opening. The openings are positioned to expose the at least one longitudinal face of the first cartridge 104 and the second cartridge 106 and allow for air to pass through the filter 100. The box frame 102 can also include a third opening in a third wall configured to allow the first cartridge 104 and second cartridge 106 to be slidably removed from or positioned within the box frame 102. The add on filter includes a removable wall 108 which can be coupled with the box frame 102 such that the third opening is covered by the wall 108. In certain embodiments, the removable wall 108 includes protrusions 110(*a*) and (*b*) configured to engage openings 112(*a*) and (*b*) in the box frame 102. The protrusions 110(*a*) and (*b*) are configured to removably coupled with the openings 112(*a*) and (*b*). The removable wall 108 and the process of coupling it with box frame 102 will be discussed below with reference to FIGS. 8(*a*) and (*b*).

The first cartridge 104 includes an ultraviolet light source for emitting a broad spectrum of ultraviolet light and a catalytic target structure mechanically coupled to the ultraviolet light source. The target catalytic structure comprises a multi-metallic catalytic and hydrophilic material, and the hydrophilic surface attracts and absorbs moisture from the surrounding air. The first cartridge will be discussed in further detail in the discussion of FIGS. 9(*a*)-(*d*) and 10(*a*)-(*d*). The second cartridge 106 can be a deep pleat replaceable filter configured to reduce odor and microbes. The second cartridge 106 can be a pleated filter with a MERV rating between 7-14. In an embodiment of the present invention, the second cartridge 106 can be a custom filter with material for specific air contaminant removal, e.g., charcoal, sulfur coated carbon for mercury removal, or potassium permanganate coated carbon for specific VOC removal.

The add on filter 100 can also include a rack 114 configured to support the first cartridge 104 within the box frame 102. The rack 114 includes two elongate members that are each pivotably coupled to the interior face of a wall of the box frame 102 at a first end. The rack 114 is configured to be approximately parallel to the faces of the walls including the first and second opening while supporting the first cartridge 104, as illustrated in FIGS. 6(a)-(c).

Figures 6A, 6B, 6C:
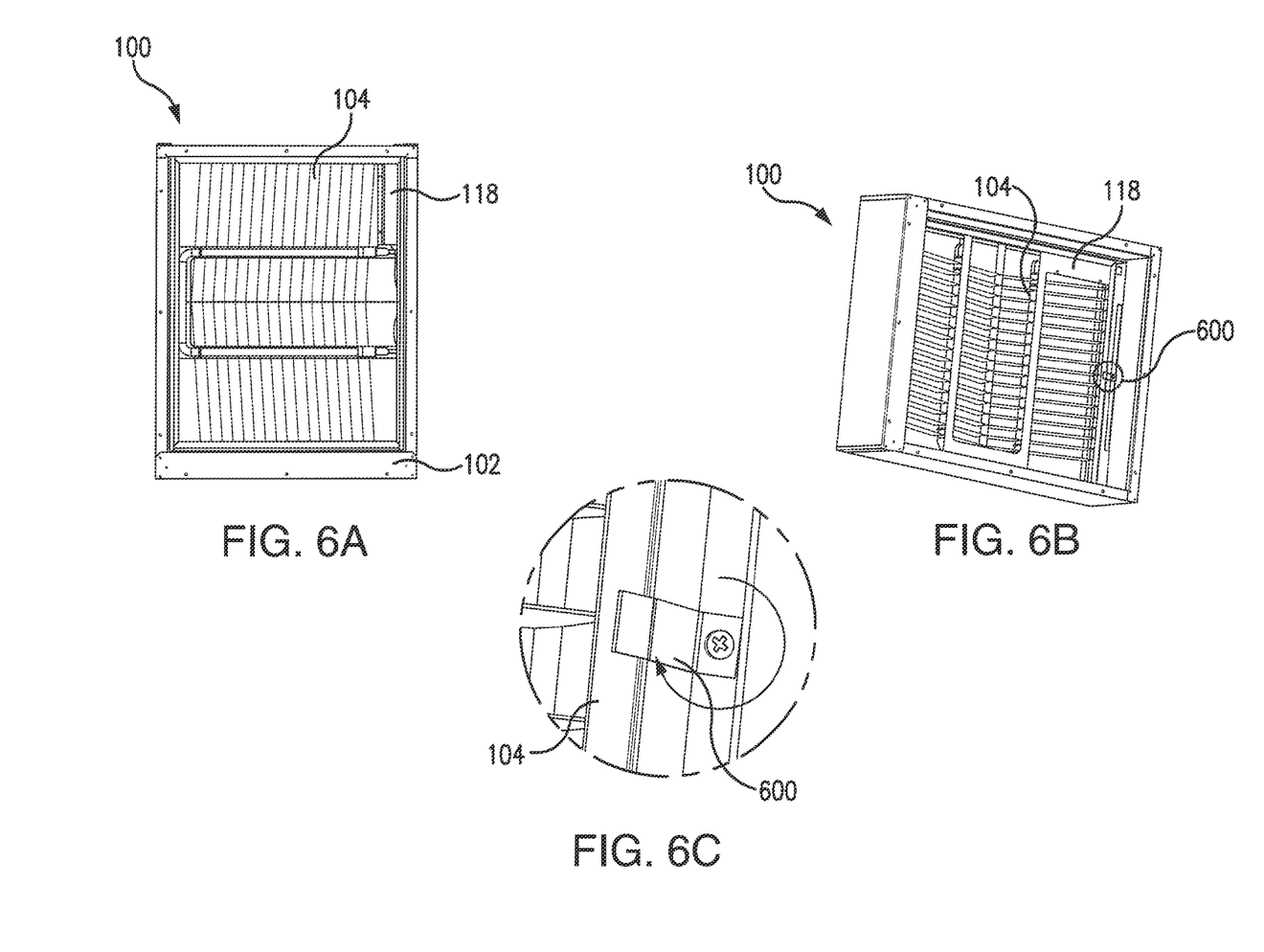
FIGS. 6(a)-(c) illustrate an add on filter in which the second cartridge has been removed in accordance with exemplary embodiments of the present invention.
Figure 7A:
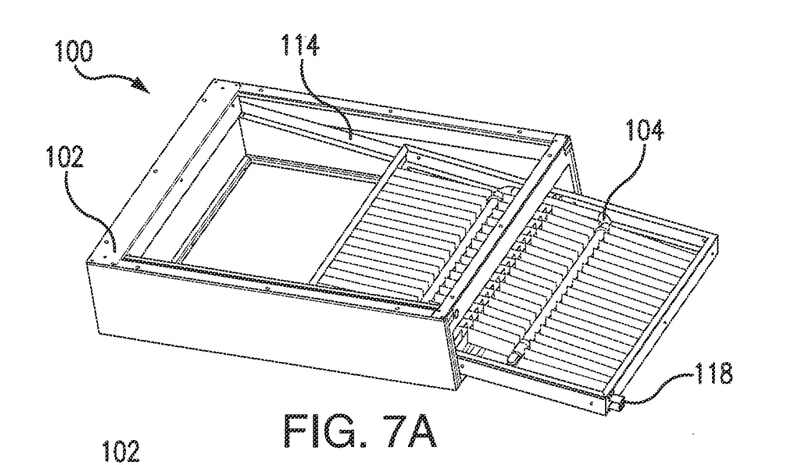
FIGS. 7(a)-(d) illustrate an add on filter configured to allow the first cartridge to be inserted or removed from the box frame in accordance with exemplary embodiments of the present invention.
Figure 7B:
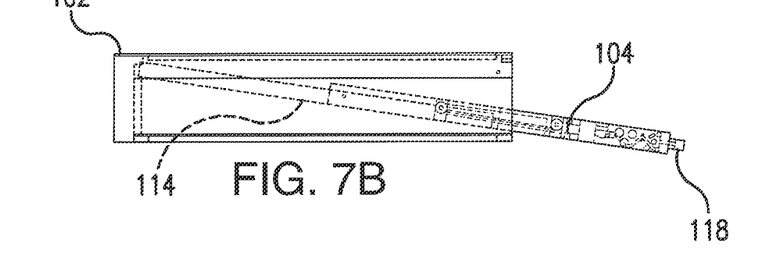
Figure 7C:
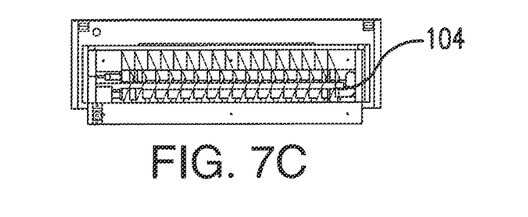
Figure 7D:
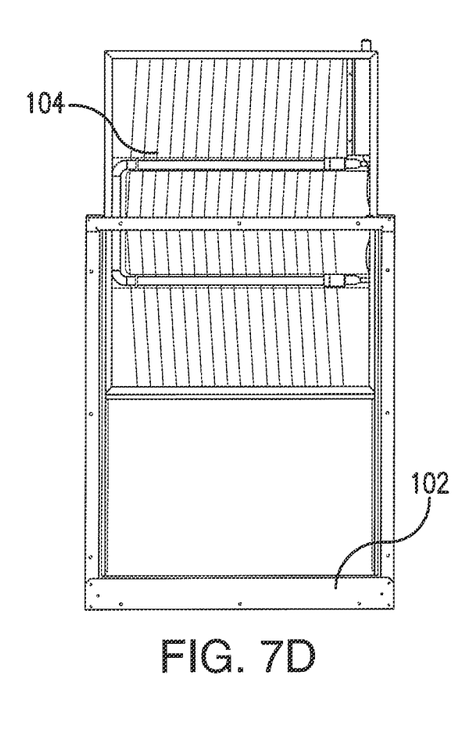

Referring now to FIGS. 6(a)-(c), the add on filter 100 can include a lock 600 for maintaining the first cartridge 104 and the rack 114 approximately parallel to the faces of the walls including the first and second opening even when the second cartridge 106 is not present to support the first cartridge 104. The rack 114 can be pivoted to allow the first cartridge 104 to be positioned within or removed from the box frame 102, as illustrated in FIGS. 2, 3 and 7(a)-(d). In this position, a second end of the rack 114 is angled downwardly such that the first cartridge 104 can be slidably removed from or placed on the rack 114.

The add on filter 100 can also include an opening 116(a)-(b) configured to allow a power source to be provided to a ballast 118 of the first cartridge 104. The opening 116(a)-(b) includes a first opening 116(a) in the box frame 102 and a second opening 116(b) in the removable wall 108. The first opening 116(a) and the second opening 116(b) are positioned such that when the removable wall 108 is coupled to the box frame 102, the first opening 116(a) and the second opening 116(b) line up and allow a power source to provide power to the ballast 118.

Figure 1:
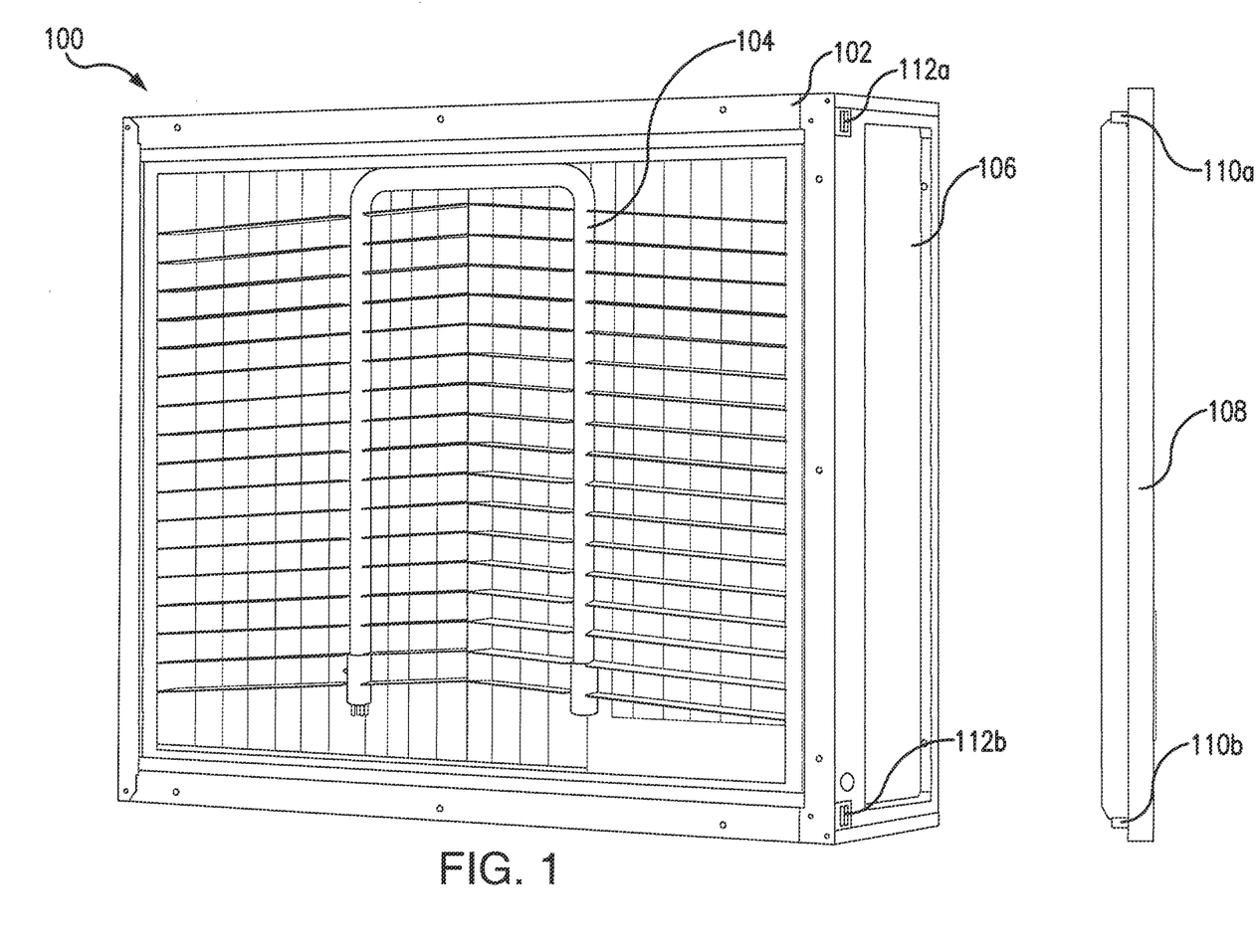
FIG. 1 is a perspective view of an add on filter in accordance with exemplary embodiments of the present invention.
Figure 2:
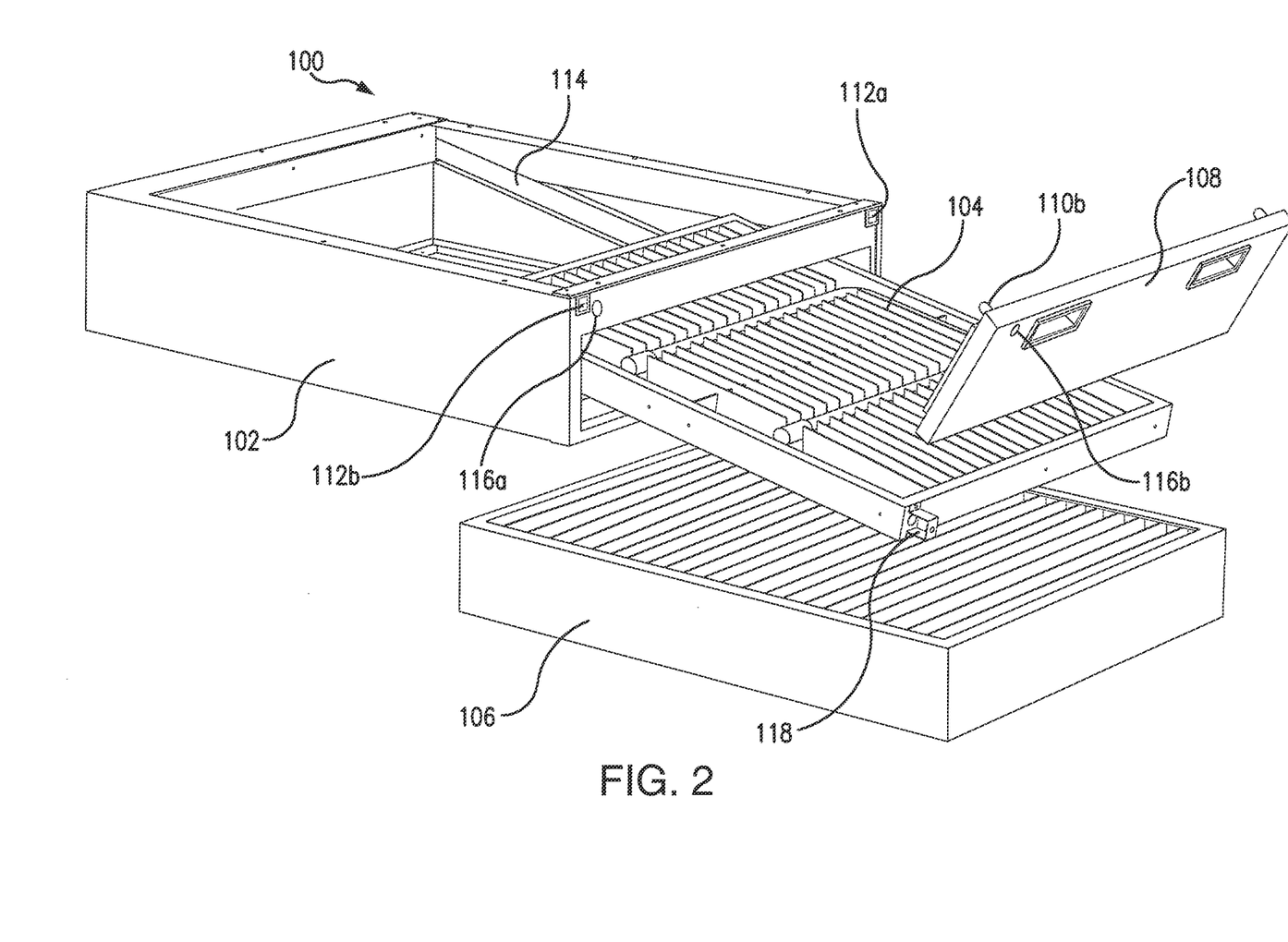
FIG. 2 is a perspective view of an exploded add on filter in accordance with exemplary embodiments of the present invention.
Figure 3:
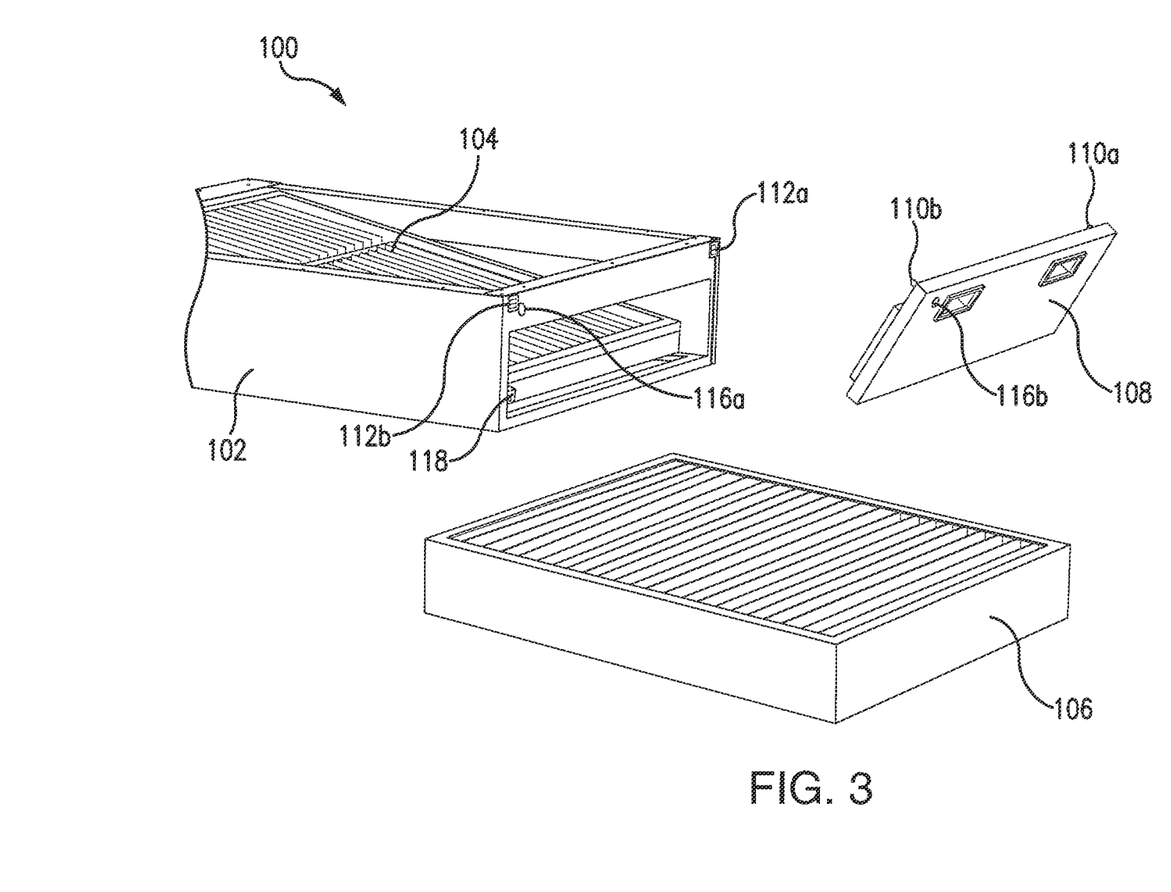
FIG. 3 is a perspective view of an exploded add on filter in accordance with exemplary embodiments of the present invention.
Figures 4A, 4B, 4C:
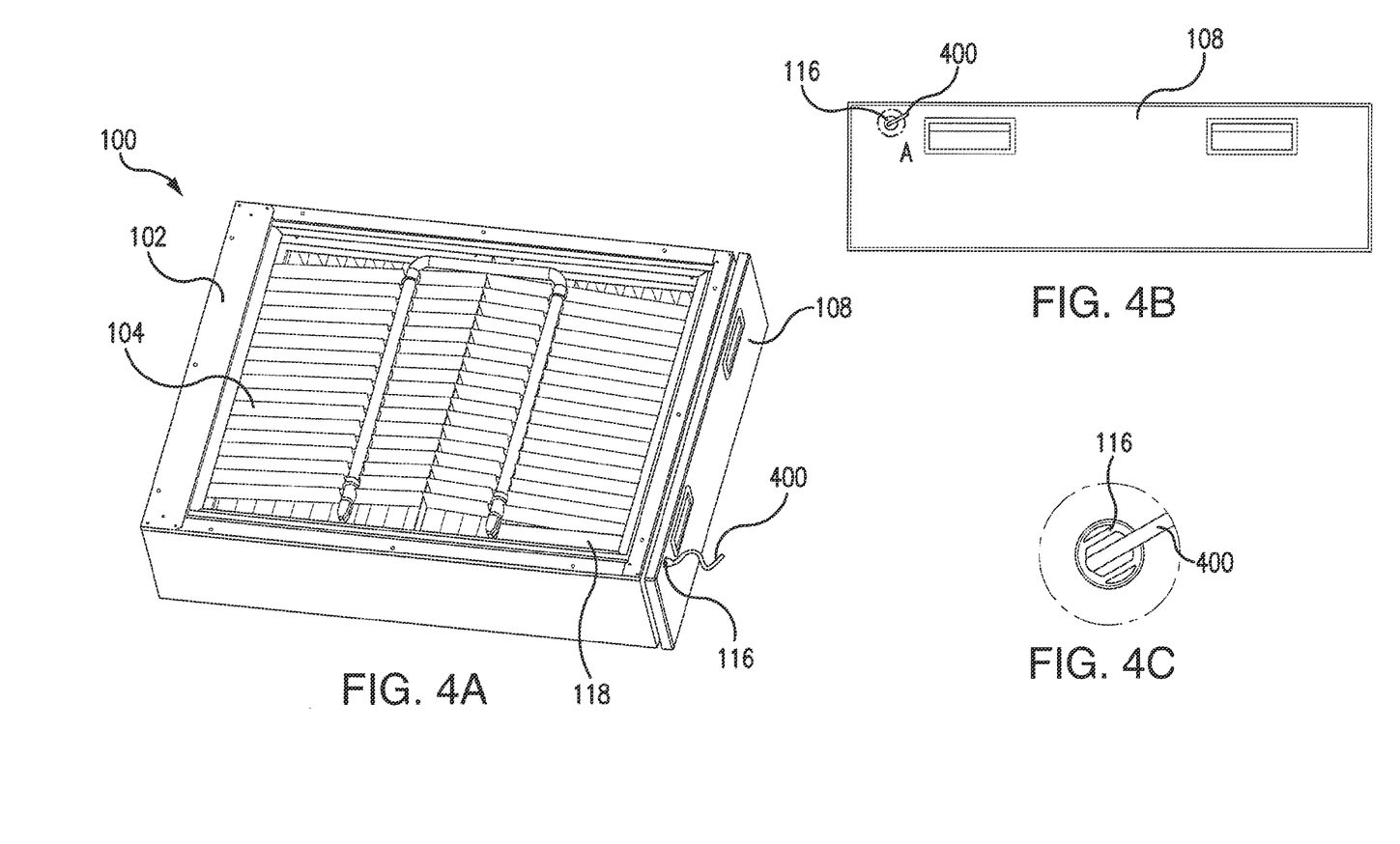
FIGS. 4(a)-(c) illustrate an assembled add on filter in accordance with exemplary embodiments of the present invention.

Referring now to FIGS. 4(a)-(c), an add on filter 100 in which an external power source 400 is providing power to the ballast 118 is shown. The external power source 400 includes a cord capable of passing through the openings 116(a) and (b) and couple with the ballast 118.

Figure 5:
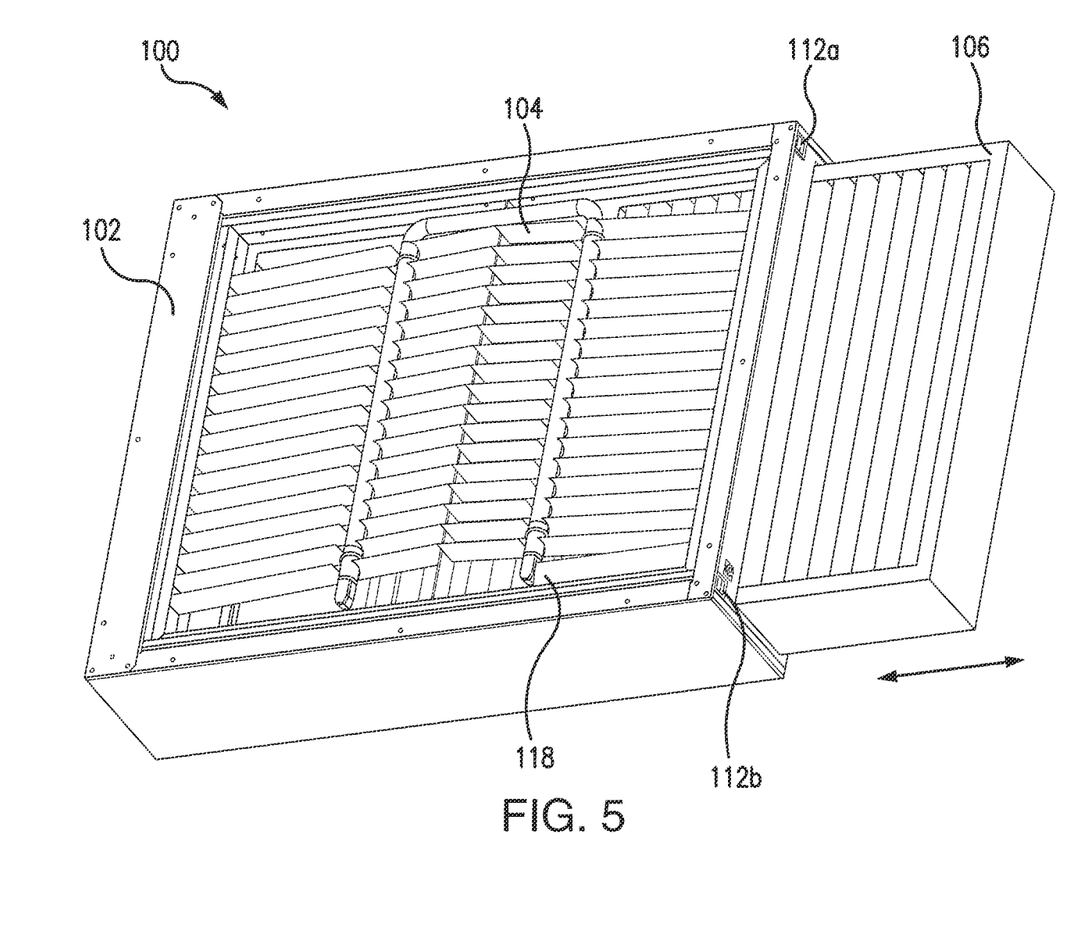
FIG. 5 illustrates a perspective view of an exploded add on filter in accordance with exemplary embodiments of the present invention.

FIG. 5 illustrates an add on filter 100 in which the removable wall 108 has been removed and the second cartridge 106 is being slidably moved in relation to the box frame 102. When the removable wall 108 is not present, the second cartridge 106 can be slid in and out of the box frame 102 through the opening exposed by the removable wall 108, the third opening.

FIGS. 6(a)-(c) illustrate an add on filter 100 in which only the first cartridge 104 is present. In an embodiment of the present invention, the add on filter 100 may be used with only the first cartridge 104, i.e., the add on filter 100 may be used without the second cartridge 106. The first cartridge 104 can be held in position by a lock 600. When the lock 600 is placed in an unlocked position, the first cartridge 104 may be slidably moved relative to the box frame 102 when the rack has been placed in a downwardly sloping position, as illustrated in FIGS. 7(a)-(d).

Figures 8A, 8B:
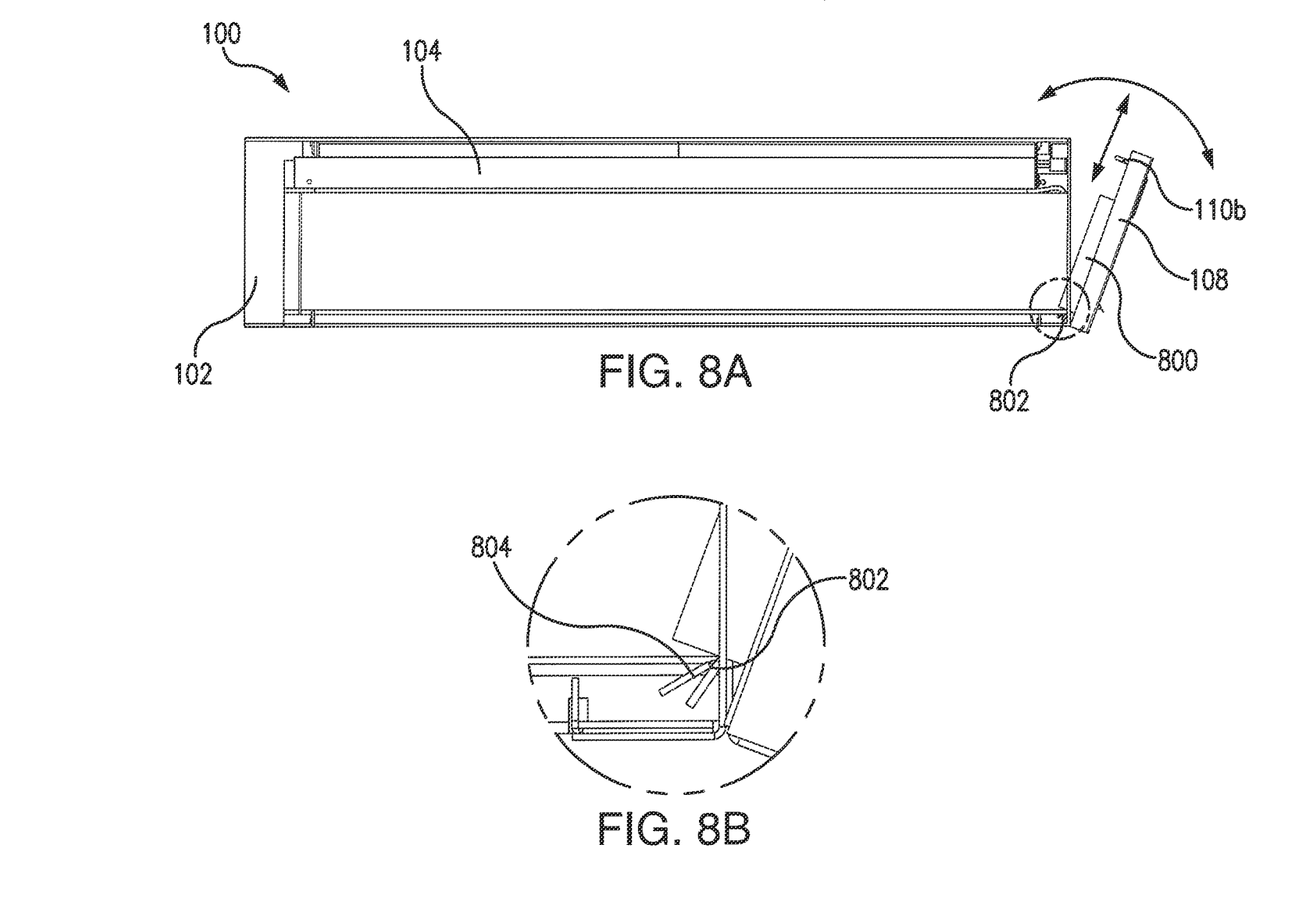
FIGS. 8(a)-(b) illustrate a detailed view of the removable wall of the add on filter box in accordance with exemplary embodiments of the present invention.
Figures 9A, 9B, 9C:
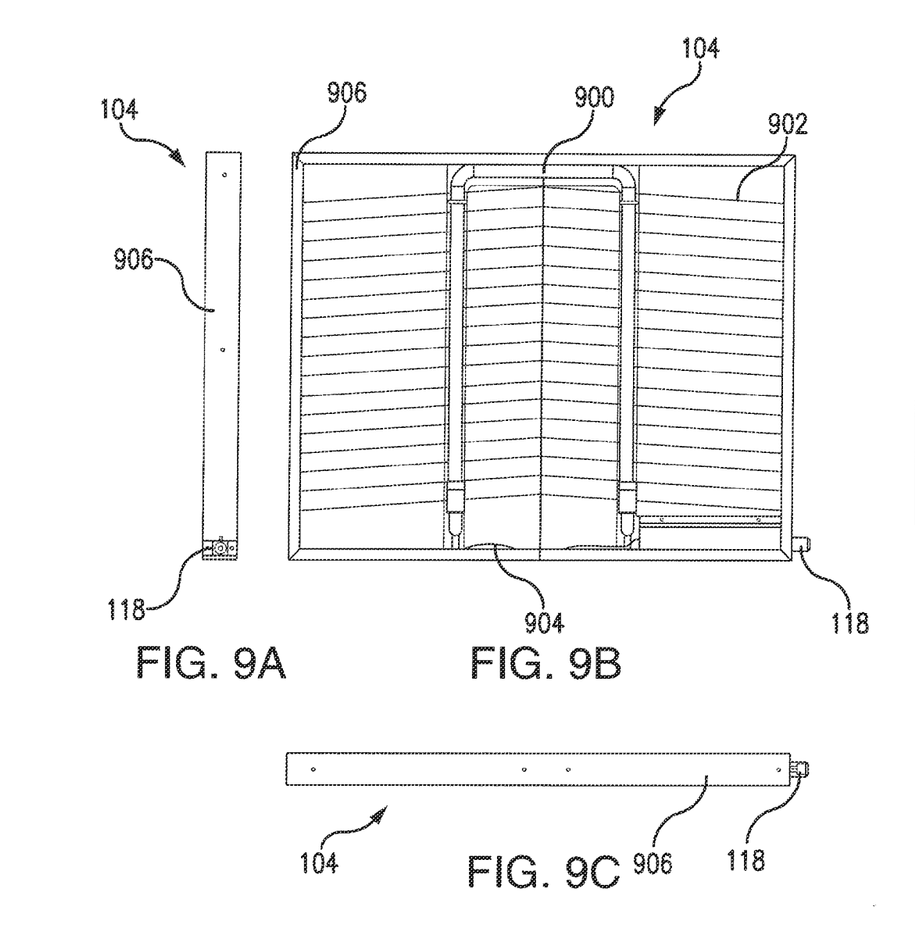
FIGS. 9(a)-(d) illustrate a first cartridge of an add on filter in accordance with exemplary embodiments of the present invention.
Figure 9D:
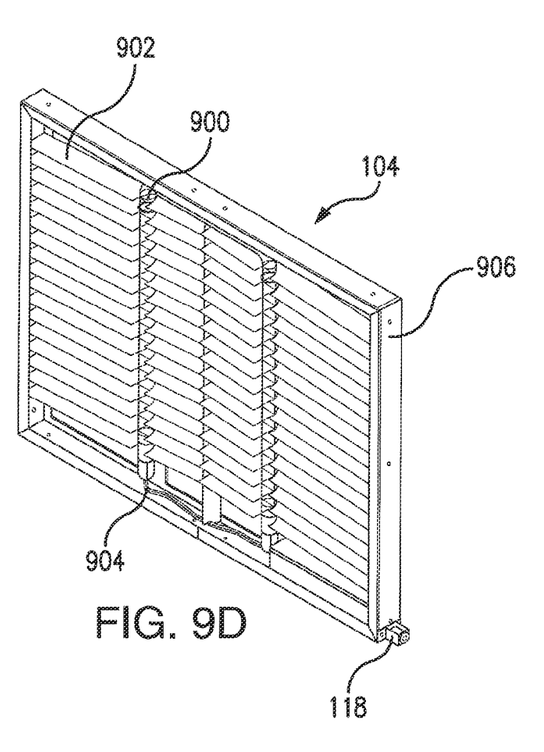
Figures 10A, 10B, 10C:
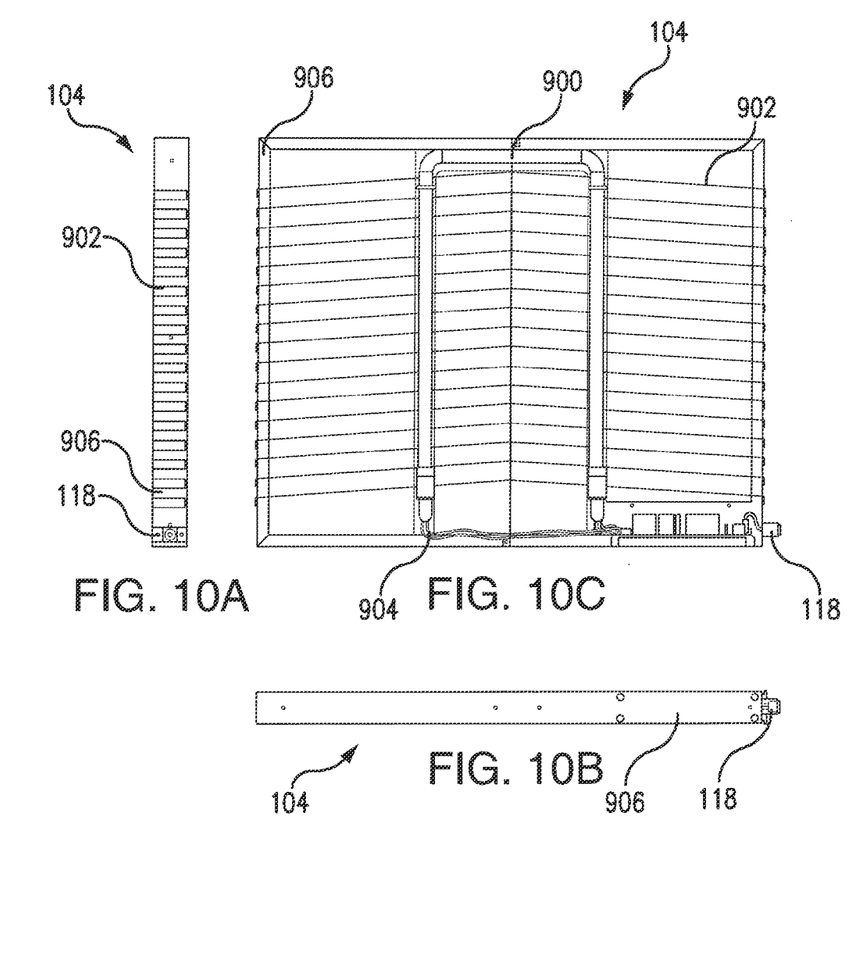
FIGS. 10(a)-(d) illustrate a first cartridge of an add on filter in accordance with exemplary embodiments of the present invention.
Figure 10D:
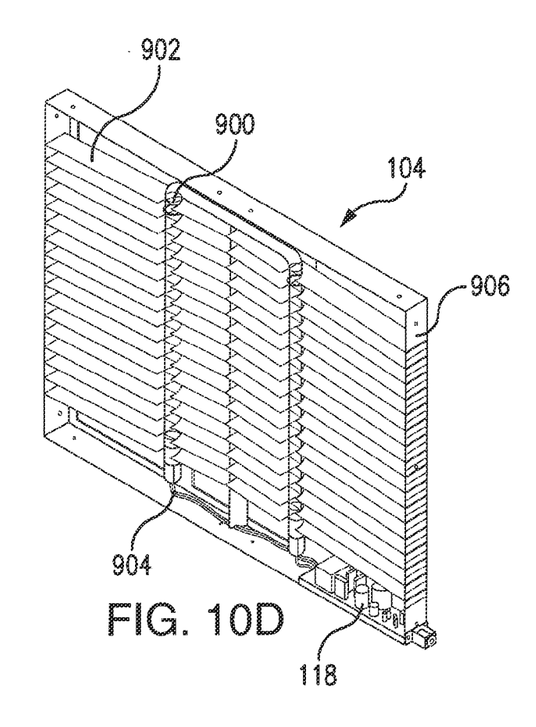

FIGS. 8(a) and (b) illustrate an add on filter 100 in which the removable wall 108 is partially coupled to the box frame 102. The removable wall 108 includes top protrusions 110, an insulative wall 800 and a bottom protrusion 802. As already discussed, the top protrusions 110(a) and (b) are configured to engage top openings 112(a) and (b) of the box frame. The bottom protrusion 802 is configured to engage a bottom opening 804 in the box frame. The bottom opening 804 is configured such that it can receive the bottom protrusion 802 and the removable wall 108 can be pivoted into a coupled position, i.e., a position in which the top protrusions 110(a) and (b) engage the top openings 112(a) and (b).

In certain embodiments of the present invention, the removable wall 108 includes a plurality of bottom protrusions 802 and the box frame 102 includes at least one bottom opening 804 for each bottom protrusion 802.

FIGS. 9(a)-(d) and 10(a)-(d) illustrate a first cartridge 104 according to certain embodiments of the present invention. The first cartridge 104 includes an ultraviolet light source 900, a target structure 902, a ballast 118, a cord 904 and a frame 906. The ultraviolet light source 900 is an approximately U-shaped bulb. This design allows for the ultraviolet light emitted by the source 900 to contact a larger surface area in a rectangular cartridge filter. The target structure 902 is designed to maximize the surface area contacted by the ultraviolet light emitted by the source 900. The target structure 902 is also designed to minimize the pressure drop of air passing through the filter caused by the structure.

The ultraviolet light source 900 emits ultraviolet light at two bands: about 254 nm wavelength and at about 185 nm wavelength. The target catalytic structure 902 comprises a multi-metallic catalytic and hydrophilic material, and the hydrophilic surface attracts and absorbs moisture from the surrounding air. The ultraviolet energy at 254 nm strikes the target structure 902 and activates production of Hydroxyl Radicals, Super Oxide ions and Hydro Peroxide on the surface. The ultraviolet energy at 185 nm is sufficient to split oxygen molecules to form ozone gas. These ozone molecules in the air are then reduced back to oxygen via decomposition process initiated by the 254 nm ultraviolet light energy, which results in the production of Hydroxyl Radicals, Super Oxide ions and Hydro Peroxide similar to the surface reaction. The ultraviolet light source 900 is supplied energy by the ballast 118 via the cord 904.

Figure 11:
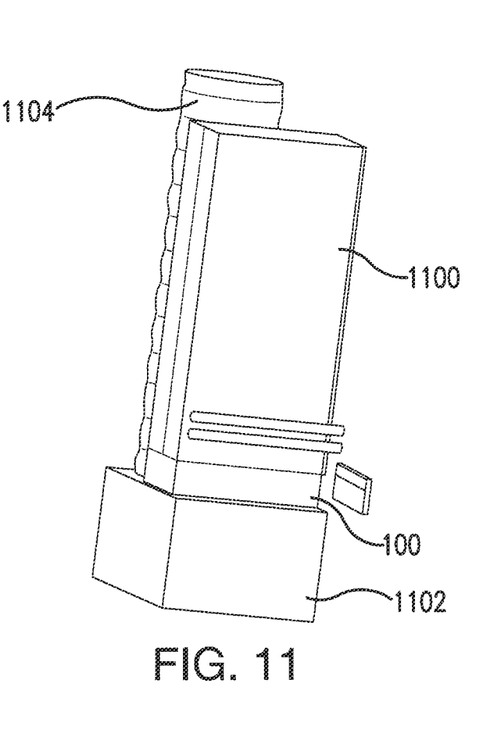
FIG. 11 illustrates a perspective view an air filtration system including an add on filter in accordance with exemplary embodiments of the present invention.
Figure 12:
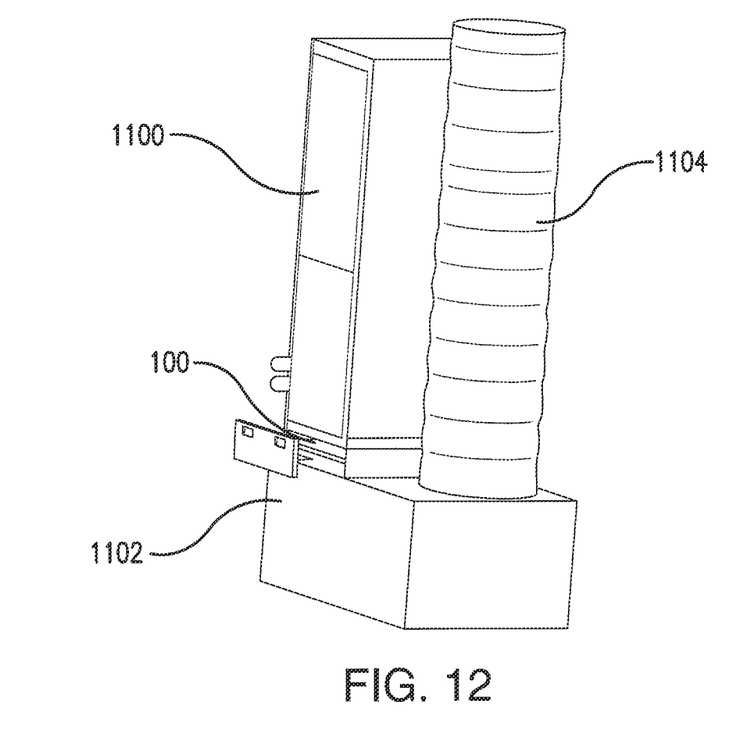
FIG. 12 illustrates a perspective view of an air filtration system including an add on filter in accordance with exemplary embodiments of the present invention.
Figure 13:
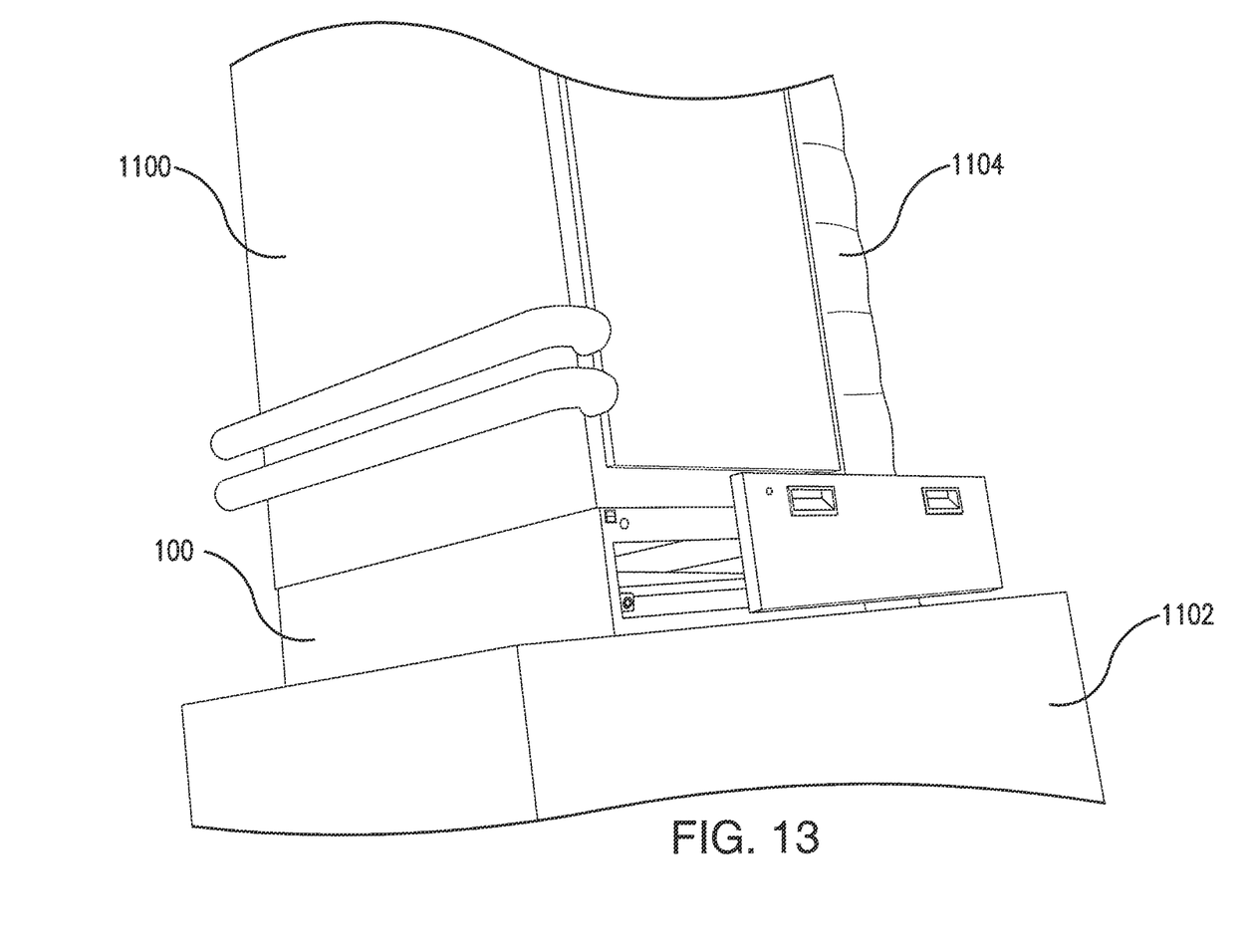
FIG. 13 illustrates a close-up view of an add on filter incorporated in an air filtration system in accordance with exemplary embodiments of the present invention.

FIGS. 11-13 illustrate the add on filter 100 in an air filtration system according to certain embodiments of the present invention. The air filtration system includes an evaporator or AC unit 1100, the add on filter 100, an air supply 1102 and an air return member 1104. The air filter system can be vertical or horizontal. The add on filter 100 is coupled to the intake end of the evaporator or AC unit 1100 and the output of the air supply 1102. In an embodiment of the present invention, the add on filter 100 can be coupled to the evaporator or AC unit 1100 by removing an access cover of the evaporator unit 1100 and screwing or otherwise coupling the evaporator unit 1100 to the add on filter 100. The add on filter 100 can be coupled to the air supply 1104 by screwing or otherwise coupling the add on filter 100 while removable wall 108 is off and the cartridges are removed. Air to be filtered and treated is provided to the add on filter 100 from the air supply 1102. As the air passes through the add on filter 100, the air is treated with advanced oxidation products which reduce odors and microbes, as discussed above. The treated air is then provided to the evaporator unit 1100 where it is further treated and then supplied to its destination (e.g., home, office, building, etc.). In an embodiment of the present invention, the air is returned from the destination (e.g., home, office, building, etc.) via the air return member 1104 and provided to the air supply 1102.

The add on filter 100 is sized to match the evaporator or AC unit 1100. The add on filter 100 can come in many different sizes to match the various evaporator or AC units 1100 on the market.

The add on filter 100 may be coupled to air filtration systems upon initial installation or added as an aftermarket item. If the add on filter 100 is added to an existing air filtration system, the evaporator or AC unit 1100 must be raised enough to accommodate the height of the add on filter 100. A portion of the ventilation, duct work or any other member the evaporator or AC unit 1100 is coupled to on its output end must be removed that is equivalent to the height of the add on filter 100. The add on filter 100 may then be coupled to the evaporator or AC unit 1100 and placed into the air filtration system.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

We claim:

1. An add on filter, comprising
    a first cartridge including an ultraviolet light source for emitting a broad spectrum of ultraviolet light and a catalytic target structure mechanically coupled to the ultraviolet light source;
    a box frame configured to be coupled with an Intake side of an air handler and further configured to house said first cartridge; and
    wherein said box frame includes two rails positioned on opposite sides of the box, wherein a first end of each of said rails is pivotably coupled to an interior side of a face of said box frame and each of said rails is configured to support said cartridge.

2. The add on filter of claim 1, further comprising a second cartridge.

3. The add on filter of claim 2, wherein said second cartridge includes a pleated filter.

4. The add on filter of claim 2, wherein said second cartridge includes charcoal.

5. The add on filter of claim 2, wherein said second cartridge includes sulfur coated carbon.

6. The add on filter of claim 2, wherein said second cartridge includes potassium permanganate coated carbon.

7. The add on filter of claim 1, wherein said box frame includes a plurality of faces and at least one of said plurality of faces is adjustable between an open and closed position.

8. The add on filter of claim 7, wherein said first cartridge is capable of being removed from or placed into said box frame when said adjustable face is in an open position.

9. The add on filter of claim 7, wherein said add on filter includes a second cartridge, and said first cartridge and said second cartridge are capable of being removed from or placed into said box frame when said adjustable face is in an open position.

10. The add on filter of claim 1, wherein said catalytic target structure includes a plurality of fin elements.

11. The add on filter of claim 1, further comprising a ballast configured to provide power to said ultraviolet light source.

12. The add on filter of claim 11, wherein said ballast includes a power connector configured to receive power from an external source and at least one of said plurality of faces of said box frame includes an opening configured to expose said power connector.

13. The add on filter of claim 1, wherein said box frame is configured to mate with an evaporator unit.

14. The add on filter of claim 1, wherein said box frame includes a latch adjustable between a locked position, in which said first cartridge and rails are held in place, and an open position in which said rails are pivotable.

15. The add filter of claim 1, wherein said box frame is comprised of insulative material.

16. A filter system, comprising:
    an evaporator including an input end and an output end;
    an add on filter including an input end and an output end, wherein said add on filter includes a box frame and a first cartridge including an ultraviolet light source for emitting a broad spectrum of ultraviolet light and a catalytic target structure mechanically coupled to the ultraviolet light source;
    wherein said output end of said add on filter is coupled to the Input end of said evaporator;
    an air supply including an output end, wherein said output end of said air supply is coupled to the input end of said add on filter; and
    wherein said box frame includes two rails positioned on opposite sides of the box, wherein a first end of each of said rails is pivotably coupled to an interior side of a face of said box frame and each of said rails is configured to support said first cartridge.

17. A filter system of claim 16, wherein said air supply includes a structure carrying air returned from a building.

* * * * *